United States Patent [19]

Drewlow et al.

[11] Patent Number: Plant 7,004

[45] Date of Patent: Aug. 29, 1989

[54] BEGONIA PLANT NAMED APPLEBLOSSOM

[75] Inventors: Lyndon W. Drewlow, Ashtabula; Arthur Barco, Medina, both of Ohio

[73] Assignee: Mikkelsens, Inc., Ashtabula, Ohio

[21] Appl. No.: 251,230

[22] Filed: Sep. 29, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new begonia plant cultivar named Appleblossom with fully double, pale pink flowers, bright green leaves with no red pigmentation in the leaf margins, vigorous growth habit with good self-branching; and floriferous habit.

1 Drawing Sheet

1

The present invention relates to a new and distinctive cultivar of begonia plant, botanically known as *hiemalis Begonia,* Fotsch, and known by the cultivar name Appleblossom.

The new cultivar was discovered by us as a mutation of Hilda (U.S. Plant Pat. No. 5,532) and observed in a group of 15 cm flowering plants of the parent cultivar. The new cultivar was initially identified as 87-7003.

Axexual reproduction of the new cultivar by stem and/or leaf cuttings by us in Ashtabula, Ohio, has reproduced the unique features of the new cultivar through successive propagations.

The following characteristics distinguish Appleblossom from its parent and other begonias commercially known and used in the floriculture industry. In describing the characteristics, reference has been made to other cultivars, including Elfe (U.S. Plant Pat. No. 4,125), Barbara (U.S. Plant Pat. No. 5,179), Aphrodite Pink (U.S. Plant Pat. No. 3,318), Hilda, Heirloom, not patented, and Guinevere (patent application pending).

1. Appleblossom has pale pink flowers which are much lighter in pink color than Elfe, Barbara, Aphrodite Pink, Heirloom and Guinevere. Hilda, of which Appleblossom is a mutation, is crimson in color.

2. Flower size of Appleblossom is larger than Elfe and Heirloom; similar in size to Hilda and Aphrodite Pink; and smaller than Barbara and Guinevere.

3. Appleblossom is more double-flowered than the single-flowered Heirloom and the double-flowered Elfe, Barbara and Aphrodite Pink. It is similar in doubleness to Hilda and less double than Guinevere.

4. Plant size and shape of Appleblossom is the same as Hilda and similar to Barbara and Guinevere. Aphrodite Pink is more trailing than Appleblossom and Elfe is more compact whereas Heirloom is a taller grower.

5. Appleblossom has no red pigmentation in the leaf margins whereas Heirloom and Aphrodite Pink have a trace in the margin. Barbara, Hilda, Guinevere, and Elfe have large amounts of red pigment in the leaf margins.

6. The underside of mature and young leaves of Appleblossom and Heirloom have no red pigmentation; Barbara has a trace of red pigmentation and Hilda, Aphrodite Pink, Guinevere and Elfe are very red in color.

7. Appleblossom has bright green leaves whereas Heirloom, Barbara and Aphrodite Pink are slightly darker green. Elfe, Hilda, and Guinevere have very dark green leaves.

2

8. Appleblossom has no red pigmentation in the stems, nodes, petioles and peduncles whereas the comparison cultivars all have red pigmentation. Hilda has the most red pigmentation.

9. Appleblossom has overlapping lower leaf lobes similar to Hilda, Heirloom and Guinevere. Barbara, Elfe and Aphrodite Pink have open lobes.

10. Appleblossom is early flowering and will flower under long day conditions.

11. The bright green leaves of Appleblossom provide an attractive background to set off the distinctive pale pink flowers.

12. There are no female flowers parts or pollen in the full double flowers of Appoeblossom.

13. The leaf and plant size of Appleblossom are balanced.

14. Appleblossom propagates readily from stem and leaf cuttings and breaks well from a pinch.

The accompanying colored photograph illustrates in perspective view the overall appearance of Appleblossom, showing the colors as true as it is reasonably possible to obtain in a colored reproduction of this type.

The following is a detailed description of my new begonia cultivar based on plants produced under commercial practices in Ashtabula, Ohio, under greenhouse conditions. The photograph was taken in March, 1988, and color references are made to The Royal Horticultural Society Colour Chart except where general color terms of ordinary dictionary significance are used.

Parentage:

Mutation from the cultivar Hilda and identified as 87-7003.

Propagation:

(A) *Type cutting.*—Leaf.

(B) *Time to root.*—days at 21° C. summer; 24 days at 21° C. winter.

(C) *Rooting habit.*—Fibrous, fine, abundant.

(D) *Stem cuttings can also be employed.*—Stem cuttings 2–3 cm long will root in 16 days at 21° C. in summer and 18 days in 21° C. in winter; roots are abundant, fine and fibrous.

(E) *Time for shoot development.*—10 weeks in summer to 13 weeks in winter to obtain shoots 4 to 5 cm long.

Plant description:

(A) *Form.*—Upright, good self-branching, stems are strong for self-support; compact, short internodes; suitable for 10 to 15 cm pot production and 25 cm hanging baskets.

(B) *Habit of growth.*—Vigorous, dense habit without opening between leaves, good basal branching; usually vegetative shoots are formed at the basal nodes and flower shoots at the higher nodes.

(C) *Foliage.*—Leaves simple; alternate, borne on strong petioles 6 mm in diameter on mature leaves. (1) Size: can vary greatly with leaf position on plant and number of shoots per plant; environment can also affect leaf size; 9 to cm across and 12 to 13 cm long when mature. (2) Shape: Ovate with lobes overlapping on mature leaves. (3) Texture: Glabrous, leathery. (4) Margin: Serrated. (5) Color: Young foliage, top side near 137A; Young foliage, under side near 137C; Mature foliage, top side near 147A; Mature foliage, under side near 146A. (6) Venation: Palmate, 7 to 8 major veins.

Flowering description:

(A) *Flowering habits.*—Flowering in racemes with an average of 4 to 6 flowers per raceme, with many racemes in bloom at one time. Flowering continues more or less indefinitely.

(B) *Natural flowering season.*—Will flower year around without controlling day length. Plants will flower earlier and more abundantly if subjected to a reduced day length of 12 hours for 3 weeks when daylengths are longer than 12 hours.

(C) *Flower bud.*—15 mm long and 20 mm wide just before opening. Tepals are entire around margins. Color near 157A just before opening under summer conditions. Near 36A with tinge of green when immature.

(D) *Flowers borne.*—On strong upright peduncles that are greenish white in color and 4–5 mm in diameter.

(E) *Quantity.*—Average of 5 flowers per peduncle. Flowers open in sequence as the raceme develops. Total number of flowers will vary with number of flowering shoots per plant.

(F) *Tepals.*—(1) Shape: Outer — almost rounded; Inner — more heart shaped. (2) Color top side in summer when opening: near 38C, fading to near 56B to 56C; underside near 56B. (3) Number of tepals: 30 or more. (4) Size of tepals: Outer — 22 mm wide and 21 mm long; Inner — 10 mm wide and 15 mm long. (5) Flower size: 5 cm in diameter, however, environment can affect size.

G. *Reproductive organs.*—(1) Stamens: None, as plant is full double with anthers appearing as petals. (2) Pistils: None observed to date.

Disease resistance:

Appleblossom has shown resistance to powdery mildew.

We claim:

1. A new and distinct cultivar of begonia plant named Appleblossom, as illustrated and described.

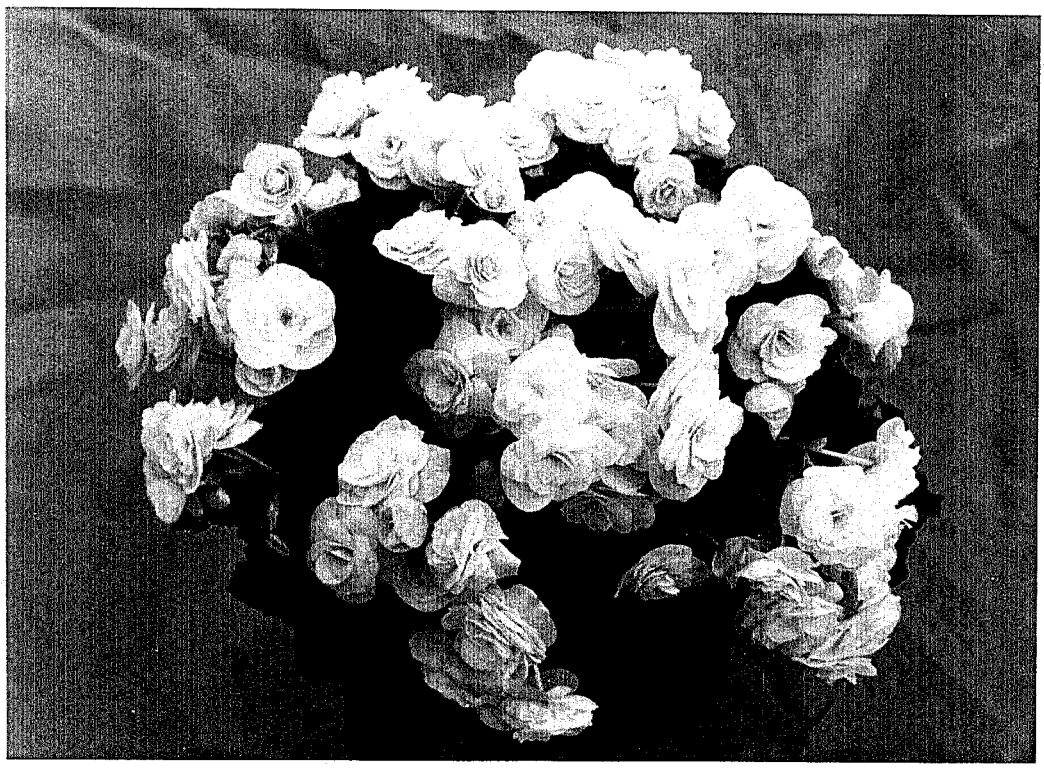

* * * * *